(12) United States Patent
Plata-Salaman et al.

(10) Patent No.: US 7,109,174 B2
(45) Date of Patent: Sep. 19, 2006

(54) ANTICONVULSANT DERIVATIVES USEFUL FOR PREVENTING THE DEVELOPMENT OF TYPE II DIABETES MELLITUS AND SYNDROME X

(75) Inventors: Carlos Plata-Salaman, Ambler, PA (US); Jeffrey Crooke, Dolyestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 77 days.

(21) Appl. No.: 10/843,134

(22) Filed: May 11, 2004

(65) Prior Publication Data

US 2004/0209824 A1    Oct. 21, 2004

Related U.S. Application Data

(63) Continuation of application No. 09/900,567, filed on Jul. 6, 2001, now Pat. No. 6,852,701.

(60) Provisional application No. 60/217,141, filed on Jul. 7, 2000, provisional application No. 60/270,022, filed on Feb. 20, 2001.

(51) Int. Cl.
*A61K 31/7012* (2006.01)
(52) U.S. Cl. .................... 514/23; 514/45.9; 514/517
(58) Field of Classification Search ............... 514/23, 514/45.9, 517
See application file for complete search history.

(56) References Cited

U.S. PATENT DOCUMENTS

| | | | |
|---|---|---|---|
| 4,513,006 | A | 4/1985 | Maryanoff et al. |
| 5,242,942 | A | 9/1993 | Costanzo et al. |
| 5,384,327 | A | 1/1995 | Costanzo et al. |
| 5,387,700 | A | 2/1995 | Maryanoff et al. |
| 6,071,537 | A | 6/2000 | Shank |
| 6,191,163 | B1 | 2/2001 | Cottrell |

FOREIGN PATENT DOCUMENTS

| | | |
|---|---|---|
| WO | WO 98/00130 A2 | 1/1998 |
| WO | WO 99/44581 A2 | 9/1999 |
| WO | WO 00/50020 A2 | 8/2000 |
| WO | WO 00/61137 A1 | 10/2000 |
| WO | WO 00/61139 A1 | 10/2000 |
| WO | WO 00/61140 A1 | 10/2000 |
| WO | WO 00/76493 A1 | 12/2000 |

OTHER PUBLICATIONS

Chengappa, R. et al "Topiramate as add-on treatment . . . " Bipolar Disorders (1999) vol. 1, pp. 42-53.*

"All About Diabetes" American Diabetes Association, http://www.diabetes.org/about-diabetes.jsp, accessed Sep. 6, 2005.*

Alberti, K. "The clinical implications of impaired glucose tolerance" Diabet. Med. (1996) vol. 13, No. 11, pp. 927-937. (abstract only).*

Crooke et al. ABSTRACT. "Topiramate Improves Glycemic Control Independent of Weight Loss in ob/ob Mice" 1 page, Jun. 2001.

Demarest et al ABSTRACT. "Topiramate Improves Glucose Tolerance and May Improve Insulin Sensitivity in Animal Models of Type 2 Diabetes Mellitus." diabetes: A Journal of the American Diabetes Association, Abstract Book, 61st Sessions, Jun. 22-26, 2001, pp. A302, vol. 50, No. Supplement 2, Philadelphia, Pennsylvania US, XP008011145.

Demarest, K. et al ABSTRACT "Topiramate Improves Tolerance and May Improve Insulin Sensitivity in Animal Models of Type 2 Diabetes Mellitus." pp. 1-10. diabetes, A Journal of the American Diabetes Association, Abstract Book, 61st Sessions, Jun. 22-26, 2001, PP.

Demarest Poster 6 Pages Figure 1a to Figure 4: diabetes, A Journal of the American Diabetes Association, Abstract Book 61st Scientific Sessions, Jun. 2226, 2001, vol. 50, Supplement 2.

Edwards, K.R. et al "Efficacy and Safety of Topiramate in the Treatment of Painful Diabetic Neuropathy: A double-blind placebo-controlled study ADIS Title: Topiramate: therapeutic use: Neurogenic pain; In patients with diabetic neuropathy" Neurology Apr. 11, 2001, vol. 54, (Suppl. 3):81, 11.

Edwards, K.R. et al "The Evaluation of Topiramate in the Management of Painful Diabetic Neuropathy." Presented at 18th Annual Meeting of the American Pain Society; Oct. 1999, Fort Lauderdale, Florida.

Osborne et al. "Topiramate Improves Glycemic Control and Triglycerides in Animal Models." diabetes: A Journal of the American Diabetes Association, Abstract Book, 61st Scientific Sessions, Jun. 22-26, 2001, pp. A302-A303, vol. 50. No. Supplement 2, Philadelphia, Pennsylvania, US, XP008011144.

Osborne Figures 4 pages: diabetes: A Journal of the American Diabetes Association, Abstract Book, 61st Scientific Sessions, Jun. 22-26, 2001, vol. 50, Supplement 2.

The Merck Manual, 1999, Merck Research, Whitehouse Station, NJ, XP002224345, Diabetes Mellitus, pp. 165-177.

York, D.A. et al "Effects of Topiramate on High Fat Diet-Induced Obesity." FASEB Journal. Fed of America Soc. for Experimental Biology, Apr. 2000, pp. A431, vol. 14, No. 4, Bethesda, Maryland, US, XP00915192.

* cited by examiner

*Primary Examiner*—Leigh C. Maier
(74) *Attorney, Agent, or Firm*—Mary A. Appollina

(57) ABSTRACT

Anticonvulsant derivatives useful for preventing the development of Type II diabetes mellitus and Syndrome X are disclosed.

5 Claims, No Drawings

ANTICONVULSANT DERIVATIVES USEFUL FOR PREVENTING THE DEVELOPMENT OF TYPE II DIABETES MELLITUS AND SYNDROME X

CROSS REFERENCE TO RELATED APPLICATIONS

This application is a continuation of U.S. application Ser. No. 09/900,567, filed Jul. 6, 2001 now U.S. Pat. No. 6,852,701, which claims priority from U.S. provisional application Ser. No. 60/217,141 filed Jul. 07, 2000 and U.S. provisional application Ser. No. 60/270,022 filed, Feb. 20, 2001, the contents of all of which are hereby incorporated by reference.

BACKGROUND OF THE INVENTION

Compounds of Formula (I):

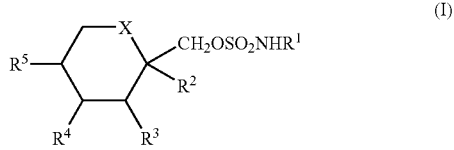

are structurally novel antiepileptic compounds that are highly effective anticonvulsants in animal tests (MARYANOFF, B. E, NORTEY, S. O., GARDOCKI, J. F., SHANK, R. P. AND DODGSON, S. P. *J. Med. Chem.* 1987, 30, 880–887; MARYANOFF, B. E., COSTANZO, M. J., SHANK, R. P., SCHUPSKY, J. J., ORTEGON, M. E., AND VAUGHT J. L. *Bioorg. Med. Chem. Lett.* 1993, 3, 2653–2656; SHANK, R. P., GARDOCKI, J. F., VAUGHT, J. L., DAVIS, C. B., SCHUPSKY, J. J., RAFFA, R. B., DODGSON, S. J., NORTEY, S. O., MARYANOFF, B. E. *Epilepsia* 1994, 35, 450–460; MARYANOFF B E, COSTANZO M J, NORTEY S O, GRECO M N, SHANK R P, SCHUPSKY J J, ORTEGON M P, VAUGHT J L. *J. Med. Chem.* 1998, 41, 1315–1343). These compounds are covered by three U.S. Pat. No. 4,513,006, U.S. Pat. No. 5,242,942, and U.S. Pat. No. 5,384,327. One of these compounds 2,3:4,5-bis-O-(1-methylethylidene)-β-D-fructopyranose sulfamate known as topiramate has been demonstrated in clinical trials of human epilepsy to be effective as adjunctive therapy or as monotherapy in treating simple and complex partial seizures and secondarily generalized seizures (E. FAUGHT, B. J. WILDER, R. E. RAMSEY, R. A. REIFE, L D. KRAMER, G. W. PLEDGER, R. M. KARIM et. al., *Epilepsia* 1995, 36 (S4), 33; S. K. SACHDEO, R. C. SACHDEO, R. A. REIFE, P. LIM and G. PLEDGER, *Epilepsia* 1995, 36 (S4), 33; T. A. GLAUSER, *Epilepsia* 1999, 40 (S5), S71–80; R. C. SACHDEO, *Clin. Pharmacokinet.* 1998, 34, 335–346), and is currently marketed for the treatment of seizures in patients with simple and complex partial epilepsy and seizures in patients with primary or secondary generalized seizures in the United States, Europe and most other markets throughout the world.

Compounds of Formula (I) were initially found to possess anticonvulsant activity in the traditional maximal electroshock seizure (MES) test in mice (SHANK, R. P., GARDOCKI, J. F., VAUGHT, J. L., DAVIS, C. B., SCHUPSKY, J. J., RAFFA, R. B., DODGSON, S. J., NORTEY, S. O., and MARYANOFF, B. E., *Epilepsia* 1994, 35, 450–460). Subsequent studies revealed that Compounds of Formula (I) were also highly effective in the MES test in rats. Topiramate was also found to effectively block seizures in several rodent models of epilepsy (J. NAKAMURA, S. TAMURA, T. KANDA, A. ISHII, K. ISHIHARA, T. SERIKAWA, J. YAMADA, and M. SASA, Eur. J. *Pharmacol.* 1994, 254, 83–89), and in an animal model of kindled epilepsy (A. WAUQUIER and S. ZHOU, *Epilepsy Res.* 1996, 24, 73–77).

More recently compounds of formula (I) have been found to be effective for maintaining weight loss, as disclosed in WIPO publication WO00/61140, for the treatment of obesity, as disclosed in U.S. Pat. No. 6,071,537 (WO 9800130), for lowering blood glucose levels, as disclosed in WIPO publication WO00/61139 and for lowering lipids as disclosed in WIPO publication WO00/61137. Thakur et al in WIPO publication WO99/44581 disclose the use of topiramate for the treatment of diabetes.

Type II diabetes mellitus (non-insulin-dependent diabetes mellitus or NIDDM) is a metabolic disorder involving dysregulation of glucose metabolism and insulin resistance, and long-term complications involving the eyes, kidneys, nerves, and blood vessels. Type II diabetes mellitus usually develops in adulthood (middle life or later) and is described as the body's inability to make either sufficient insulin (abnormal insulin secretion) or its inability to effectively use insulin (resistance to insulin action in target organs and tissues). More particularly, patients suffering from Type II diabetes mellitus have a relative insulin deficiency. That is, in these patients, plasma insulin levels are normal to high in absolute terms, although they are lower than predicted for the level of plasma glucose that is present.

Type II diabetes mellitus is characterized by the following clinical signs or symptoms: persistently elevated plasma glucose concentration or hyperglycemia; polyuria; polydipsia and/or polyphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Syndrome X, also termed Insulin Resistance Syndrome (IRS), Metabolic Syndrome, or Metabolic Syndrome X, is a disorder that presents risk factors for the development of Type II diabetes mellitus and cardiovascular disease including glucose intolerance, hyperinsulinemia and insulin resistance, hypertriglyceridemia, hypertension and obesity.

The diagnosis of Type II diabetes mellitus includes assessment of symptoms and measurement of glucose in the urine and blood. Blood glucose level determination is necessary for an accurate diagnosis. More specifically, fasting blood glucose level determination is a standard approach used. However, the oral glucose tolerance test (OGTT) is considered to be more sensitive than fasted blood glucose level. Type II diabetes mellitus is associated with impaired oral glucose tolerance (OGT). The OGTT thus can aid in the diagnosis of Type II diabetes mellitus, although generally not necessary for the diagnosis of diabetes (Emancipator K, Am J Clin Pathol 1997 November ;112(5):665–74; Type 2 Diabetes Mellitus, Decision Resources Inc., March 2000). The OGTT allows for an estimation of pancreatic beta-cell secretory function and insulin sensitivity, which helps in the diagnosis of Type II diabetes mellitus and evaluation of the severity or progression of the disease (e.g., Caumo A, Bergman R N, Cobelli C, J Clin Endocrinol Metab 2000, 85(11):4396–402). More particularly, the OGTT is extremely helpful in establishing the degree of hyperglycemia in patients with multiple borderline fasting blood glucose levels that have not been diagnosed as diabetics. In addition, the OGTT is useful in testing patients with symptoms of Type II diabetes mellitus where the possible diagnosis of abnormal carbohydrate metabolism has to be clearly established or refuted.

Thus, impaired glucose tolerance is diagnosed in individuals that have fasting blood glucose levels less than those required for a diagnosis of Type II diabetes mellitus, but have a plasma glucose response during the OGTT between normal and diabetics. Impaired glucose tolerance is considered a prediabetic condition, and impaired glucose tolerance (as defined by the OGTT) is a strong predictor for the development of Type II diabetes mellitus (Haffner S M, Diabet Med 1997 August ; 14 Suppl 3:S12–8).

Type II diabetes mellitus is a progressive disease associated with the reduction of pancreatic function and/or other insulin-related processes, aggravated by increased plasma glucose levels. Thus, Type II diabetes mellitus usually has a prolonged prediabetic phase and various pathophysiological mechanisms can lead to pathological hyperglycemia and impaired glucose tolerance, for instance, abnormalities in glucose utilization and effectiveness, insulin action and/or insulin production in the prediabetic state (Goldberg R B, Med Clin North Am 1998 July ;82(4):805–21).

The prediabetic state associated with glucose intolerance can also be associated with a predisposition to abdominal obesity, insulin resistance, hyperlipidemia, and high blood pressure, that is, Syndrome X (Groop L, Forsblom C, Lehtovirta M, Am J Hypertens 1997 September ;10(9 Pt 2):172S–180S; Haffner S M, J Diabetes Complications 1997 March-April, 11(2):69–76; Beck-Nielsen H, Henriksen J E, Alford F, Hother-Nielson O, Diabet Med 1996 September ; 13(9 Suppl 6):S78–84).

Thus, defective carbohydrate metabolism is pivotal to the pathogenesis of Type II diabetes mellitus and impaired glucose tolerance (Dinneen S F, Diabet Med 1997 August ; 14 Suppl 3:S19–24). In fact, a continuum from impaired glucose tolerance and impaired fasting glucose to definitive Type II diabetes mellitus exists (Ramlo-Halsted B A, Edelman S V, Prim Care 1999 December ; 26(4):771–89).

Early intervention in individuals at risk to develop Type II diabetes mellitus, focusing on reducing the pathological hyperglycemia or impaired glucose tolerance may prevent or delay the progression towards Type II diabetes mellitus and associated complications and/or Syndrome X. Therefore, by effectively treating impaired oral glucose tolerance and/or elevated blood glucose levels, one can prevent or inhibit the progression of the disorder to Type II diabetes mellitus or Syndrome X.

Many anti-diabetic agents typically prescribed for the treatment of Type II diabetes mellitus and/or Syndrome X, for example, sulfonylureas and thiazolidinediones, have an undesired side effect of increasing body weight. Increased body weight in patients with prediabetic conditions or with diagnosed Type II diabetes mellitus or Syndrome X results in deleterious effects due to accentuation of the metabolic and endocrine dysregulation, and obesity per se is a pivotal risk factor for the development and progressive worsening of Type II diabetes mellitus. Thus it is desirable to have an anti-diabetic agent which maintains or lowers body weight.

DISCLOSURE OF THE INVENTION

It has now been found that compounds of the following formula (I):

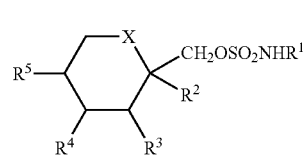

wherein X is O or $CH_2$, and $R^1$, $R^2$, $R^3$, $R^4$ and $R^5$ are as defined hereinafter are useful in preventing the development of Type II diabetes mellitus and Syndrome X.

DETAILED DESCRIPTION OF THE PREFERRED EMBODIMENTS

The sulfamates of the invention are of the following formula (I):

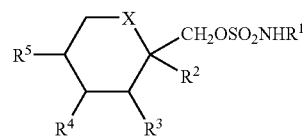

wherein
X is $CH_2$ or oxygen;
$R^1$ is hydrogen or alkyl; and
$R^2$, $R^3$, $R^4$ and $R^5$ are independently hydrogen or lower alkyl and, when X is $CH_2$, $R^4$ and $R^5$ may be alkene groups joined to form a benzene ring and, when X is oxygen, $R^2$ and $R^3$ and/or $R^4$ and $R^5$ together may be a methylenedioxy group of the following formula (II):

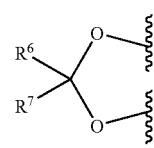

wherein
$R^6$ and $R^7$ are the same or different and are hydrogen, lower alkyl or are alkyl and are joined to form a cyclopentyl or cyclohexyl ring.

$R_1$ in particular is hydrogen or alkyl of about 1 to 4 carbons, such as methyl, ethyl and iso-propyl. Alkyl throughout this specification includes straight and branched chain alkyl. Alkyl groups for $R^2$, $R^3$, $R^4$, $R^5$, $R^6$ and $R^7$ are of about 1 to 3 carbons and include methyl, ethyl, iso-propyl and n-propyl. When X is $CH_2$, $R^4$ and $R^5$ may combine to form a benzene ring fused to the 6-membered X-containing ring, i.e., $R^4$ and $R^5$ are defined by the alkatrienyl group =C—CH=CH—CH=.

A particular group of compounds of formula (I) is that wherein X is oxygen and both $R^2$ and $R^3$ and $R^4$ and $R^5$ together are methylenedioxy groups of the formula (II), wherein $R^6$ and $R^7$ are both hydrogen both alkyl or combine to form a spiro cyclopentyl or cyclohexyl ring, in particular where $R^6$ and $R^7$ are both alkyl such as methyl. A second group of compounds is that wherein X is $CH_2$ and $R^4$ and $R^5$ are joined to form a benzene ring. A third group of compounds of formula (I) is that wherein both $R^2$ and $R^3$ are hydrogen.

The compounds of formula (I) may be synthesized by the following methods:

(a) Reaction of an alcohol of the formula $RCH_2OH$ with a chlorosulfamate of the formula $ClSO_2NH_2$ or $ClSO_2NHR^1$ in the presence of a base such as potassium t-butoxide or sodium hydride at a temperature of about −20° to 25° C. and in a solvent such as toluene, THF, or dimethylformamide wherein R is a moiety of the following formula (III):

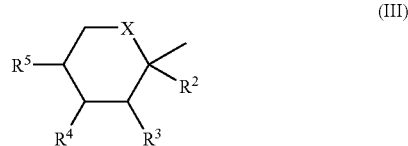

(III)

(b) Reaction of an alcohol of the formula $RCH_2OH$ with sulfurylchloride of the formula $SO_2Cl_2$ in the presence of a base such as triethylamine or pyridine at a temperature of about −40° to 25° C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R^1NH^2$ at a temperature of abut 40° to 25° C. in a solvent such as methylene chloride or acetonitrile to produce a compound of formula (I). The reaction conditions for (b) are also described by T. Tsuchiya et al. in *Tetrahedron Lett.*, 1978, 3365.

(c) Reaction of the chlorosulfate $RCH_2OSO_2Cl$ with a metal azide such as sodium azide in a solvent such as methylene chloride or acetonitrile yields an azidosulfate of the formula $RCH_2OSO_2N_3$ as described by M. Hedayatullah in *Tetrahedron Lett.* 1975, 2455. The azidosulfate is then reduced to a compound of formula (I) wherein $R^1$ is hydrogen by catalytic hydrogenation, e.g. with a noble metal and $H_2$ or by heating with copper metal in a solvent such as methanol.

The starting materials of the formula $RCH_2OH$ may be obtained commercially or as known in the art. For example, starting materials of the formula $RCH_2OH$ wherein both $R^2$ and $R^3$ and $R^4$ and $R^5$ are identical and are of the formula (II) may be obtained by the method of R. F. Brady in *Carbohydr. Res.* 1970, 14, 35 or by reaction of the trimethylsilyl enol ether of a $R^6COR^7$ ketone or aldehyde with fructose at a temperature of about 25° C., in a solvent such a halocarbon, e.g. methylene chloride in the presence of a protic acid such as hydrochloric acid or a Lewis Acid such as zinc chloride. The trimethylsilyl enol ether reaction is described by G. L. Larson et al. in *J. Org. Chem.* 1973, 38, 3935.

Further, carboxylic acids and aldehydes of the formulae RCOOH and RCHO may be reduced to compounds of the formula $RCH_2OH$ by standard reduction techniques, e.g. reaction with lithium aluminum hydride, sodium borohydride or borane-THF complex in an inert solvent such a diglyme, THF or toluene at a temperature of about 0° to 100° C., e.g. as described by H. O. House in "Modern Synthetic Reactions", 2nd Ed., pages 45 to 144 (1972).

The compounds of formula I: may also be made by the process disclosed U.S. Pat. Nos. 4,513,006, 5,242,942, and No. 5,384,327, which are incorporated by reference herein.

The compounds of formula (I) include the various individual isomers as well as the racemates thereof, e.g., the various alpha and beta attachments, i.e., below and above the plane of the drawing, of $R^2$, $R^3$, $R^4$ and $R^5$ on the 6-membered ring. Preferably, the oxygen of the methylenedioxy group (II) are attached on the same side of the 6-membered ring.

The following Examples are set forth to aid in the understanding of the invention, and are not intended and should not be construed to limit in any way the invention set forth in the claims which follow thereafter.

EXAMPLE 1

It is known that ob/ob mice when allowed to eat ad libitum, develop abnormally high blood levels of insulin (hyperinsulinemia), glucose (hyperglycemia), lesions of the skin, and a high level of glycosylated hemoglobin, all of which are hallmark signs of Type II diabetes mellitus (R. R. HENRY, *Ann. Intern. Med.* 1996, 124, 97–103; G. W. EDELSON, *Clin. Podiatr. Med. Surg.* 1998, 15, 41–48; P. R. JOHNSON, M. R. GREENWOOD, B. A. HORWITZ and J. S. STERN, *Annu. Rev. Nutr.* 1991, 11, 325–353). Based on this knowledge of the ob/ob mouse model, two studies were designed to determine the effect of compounds of formula (I) in these mice models.

In the first study, a uniform population of mice was divided into three groups; in one group of control mice no topiramate was added to the food for the entire 120-day study period. In a second group topiramate was added to the food in amounts sufficient to give a daily dose of 20 mg/kg for 84 days, then a daily dose of 180 mg/kg for 36 days. A third group received a daily dose of 60 mg/kg for the entire 120 days. After completion of the 120-day period, the mice were sacrificed and blood was obtained and prepared for subsequent analyses of glucose, insulin and triglycerides in plasma.

A statistical analysis of the results revealed that glucose was significantly lower in both groups of mice treated with topiramate than in the control group (Table 1). Insulin levels were also lower in both groups of mice treated with topiramate but the difference was statistically significant only in the first group (Table 1).

TABLE 1

Effect of topiramate on blood glucose, insulin and triglycerides in ob/ob mice

| Treatment Group (N) | TPM dose (mg/kg/day) | Blood concentration of specified marker | | |
|---|---|---|---|---|
| | | Glucose (mg/dL ± SEM) | Insulin (ng/mL ± SEM) | Triglycerides (mg/dL ± SEM |
| Control (10) | 0: 120 days | 302 ± 36 | 10.2 ± 0.5 | 190 ± 48 |
| TPM 1 (10) | 20: 84 days 180: 36 days | 183 ± 33 (−39%) P = 0.02 | 6.4 ± 0.7 (−37%) P = 0.0004 | 103 ± 5 (−46%) P = 0.075 |

TABLE 1-continued

Effect of topiramate on blood glucose, insulin and triglycerides in ob/ob mice

| Treatment Group (N) | TPM dose (mg/kg/day) | Blood concentration of specified marker | | |
|---|---|---|---|---|
| | | Glucose (mg/dL ± SEM) | Insulin (ng/mL ± SEM) | Triglycerides (mg/dL ± SEM |
| TPM 2* (10) | 60: 120 days | 179 ± 11 (−41%) P = 0.007 | 8.0 ± 0.9 (−21%) P = 0.058 | 113 ± 8 (−41%) P = 0.099 |

P values were calculated using Student's two-tailed t-test.
All P values were obtained from a comparison of the topiramate (TPM)-treated groups to the control group.
*, Body weights at the beginning of topiramate administration and at the end of the study (that is following 120 days of treatment with topiramate in the food) were similar in the control and topiramate-treated groups: 48.2 ± 1.1 g on day −1 for the control group and 48.4 ± 0.9 on day −1 for the TPM 2 group; and 62.7 ± 1.4 g on day 119 for the control group and 62.2 ± 1.2 on day 119 for the TPM 2 group.
Body weight gain for the control and TPM 2 groups from day −1 to day 119 was also similar.
Percentage differences in parentheses are versus control values.

In the second study, a uniform population of mice was divided into two groups. In one group of control mice, no topiramate was added to the food for the entire 118-day period. In a second group, topiramate was added to the food in amounts sufficient to give a daily dose of 60 mg/kg for 6 days, then a daily dose of 180 mg/kg for 112 days. During the course of the dosing period the mice were examined two-times a week for skin lesions. When skin lesions were evident, the severity was estimated based on the number and size of the lesions, and given a score ranging from mild to severe (Table 2). For four of the control mice their health deteriorated to the point that they either died or had to be euthanized. Three of these four control mice had lesions (two mice were classified as severe and one mice as mild). In addition to the four control mice that did not survive the 118-day period, other mice developed skin lesions ranging from mild to severe by the end of the study (Table 2). By comparison none of the nine mice treated with topiramate ever developed skin lesions (Table 2). After the 118-day period was completed, all surviving mice were sacrificed and blood was obtained and prepared for subsequent analysis of plasma glucose and insulin, and glycosylated hemoglobin. In this second study, the level of blood glucose was significantly lower in the topiramate-treated mice relative to the control mice (P<0.05, 276±49 mg/dL mean±SEM, n=7 for the control group and 131±13 mg/dL mean±SEM, n=9 for the topiramate-treated group at the end of the study; the difference between groups is 52%), whereas insulin levels did not differ between the two groups. Glycosylated hemoglobin was significantly higher in the surviving control mice than in the topiramate-treated mice (6.09±0.8 (n=7) versus 3.16±0.1 (n=9), mean±SEM, P<0.01, 48% reduction with topiramate treatment). Also, throughout the 118 days of study 2, the average body weight of the two groups of mice did not differ, that is, on day −1 body weights were 43.6±0.8 g (n=7) for the control group and 42.8±1.1 g (n=9) for the topiramate-treated group; and 55.2±2.4 g on day 118 for the control group and 55.1±1.3 g on day 118 for the topiramate-treated group. The body weight gain was similar in both groups throughout the study. Therfore, the beneficial effects of topiramate on the biological markers of the disease cannot be secondary to the potential beneficial effect that might arise from a loss of body eight. The data suggest that topiramate redirects metabolic and endocrine activities to improve the diabetic syndrome in the ob/ob mice, activities that are independent of topiramate's effect on body weight.

TABLE 2

Skin lesions in control and topiramate-treated ob/ob mice

| CONTROL | | | | TOPIRAMATE (180 mg/kg/day) | | | | |
|---|---|---|---|---|---|---|---|---|
| Severe | Moderate | Mild | Total | Severe | Moderate | Mild | Total | Day |
| | | | n = 7 | | | | N = 9 | |
| 1 | 1 | 1 | 3 | 0 | 0 | 0 | 0 | 118 |
| 1 | 1 | 2 | 4 | 0 | 0 | 0 | 0 | 105 |
| | | | n = 8 | | | | N = 9 | |
| 2 | 0 | 3 | 5 | 0 | 0 | 0 | 0 | 97 |
| | | | n = 9 | | | | N = 9 | |
| 2 | 1 | 3 | 6 | 0 | 0 | 0 | 0 | 96 |
| 0 | 1 | 3 | 4 | 0 | 0 | 0 | 0 | 83 |
| | | | n = 10 | | | | N = 9 | |
| 0 | 1 | 1 | 2 | 0 | 0 | 0 | 0 | 70 |
| | | | n = 11 | | | | N = 9 | |
| 0 | 0 | 2 | 2 | 0 | 0 | 0 | 0 | 61 |
| 0 | 0 | 2 | 2 | 0 | 0 | 0 | 0 | 53 |
| 0 | 0 | 0 | 0 | 0 | 0 | 0 | 0 | 41 |

For each mouse, lesions were scored as: none observed.
Mild: one or two small lesions (less than 5 mm in the longest dimension).
Moderate: one or multiple lesions (more than 5 mm but less than 8 mm in the longest dimension).
Severe: multiple lesions (more than 8 mm in the longest dimension). Day indicates the day during the 118-day period.

Thus when ob/ob mice were given topiramate admixed into food over a period of four months, the blood levels of glucose and insulin, and the level of glycosylated hemgobin were significantly lower than in control ob/ob mice not given topiramate. Furthermore, none of the mice that received topiramate at a dose of 180 mg/kg developed lesions of the skin, whereas control ob/ob mice developed lesions. These results demonstrate that topiramate either reduced or prevented the development of all the hallmark signs of Type II diabetes mellitus in an obese-diabetic animal model, even when body weight was not affected. The results also suggest that topiramate can reduce cellular resistance to insulin. This is known to be a primary factor in Type II diabetes mellitus (R. R. HENRY, *Ann. Intern. Med.*

1996, 124, 97–103; J. D. McGARRY, *Am. J. Clin. Nutr.* 1998, 67, 500S–504S; J. M. OLEFSKY and J. J. NOLAN, *Am. J. Clin. Nutr.* 1995, 61, 980S–986S).

Syndrome X, also termed Insulin Resistance Syndrome (IRS), Metabolic Syndrome, or Metabolic Syndrome X, is a disorder that presents risk factors for the development of Type 2 diabetes mellitus and cardiovascular disease including glucose intolerance, hyperinsulinemia and insulin resistance, and dyslipidemia (eg, high triglycerides). When ob/ob mice were given topiramate admixed into food over a period of four months, the blood levels of glucose, insulin, and triglycerides were significantly lower than in control ob/ob mice not given topiramate. These results demonstrate that topiramate can reduce or prevent pathophysiological signs associated with Syndrome X and thus prevent its development.

EXAMPLE 2

Six to seven week old female C57 BLK SIJ-m+/+ Lepr$^{db}$ mice (db/db) and heterozygous littermates were purchased from The Jackson Laboratory (Bar Harbor, Me.). Upon arrival the mice were quarantined for 5 days and housed in pairs in shoe-box cages containing ALPHA-dri® bedding (Shepherd Speciality Papers, Inc., Kalamazoo, Mich.). The mice were maintained at an ambient temperature of 21 to 23° C. on a 12 hour-12 hour light-dark schedule and given access to water and food ad libitum. The diet was comprised of NIH (National Institutes of Health) Rat and Mouse/Auto 6F Reduced Fat Diet No. 5K52 (PMI Nutrition International Inc., Brentwood, Mo.).

The vehicle, used as a reference and for test compounds, was 0.5% methylcellulose dissolved in water. The compounds were either fully dissolved or uniformly suspended in the vehicle when administered to the mice.

The db/db mice were randomly separated into five groups of eight, as were the heterozygous littermates. The groups were as follows: one vehicle control group and four groups that each received one of four doses of topiramate (TPM) (10, 30, 100, or 300 mg/kg, respectively). Topiramate or vehicle was administered orally by gavage once a day during the 8$^{th}$ hour of the light portion of the light-dark cycle.

Between 18 and 24 hours after the last dose was administered, the mice were anesthetized with $CO_2/O_2$ (70:30) and blood from the retro-orbital sinus puncture was collected into 2 mL heparinized snap-top polypropylene tubes, then placed in ice.

Plasma was separated from blood cells by centrifugation (15 minutes at 1600 g). For samples not assayed immediately, the plasma was transferred into 96-well plates and frozen at −70° C.

Glucose and triglycerides were assayed using standard procedures for blood clinical laboratories. Specifically, the samples were analyzed using an automated Hitachi 717 autoanalyzer (Boehringer Mannheim/Hitachi 717 Autoanalyzer, Boehringer Mannheim Laboratory Systems Division, Indianapolis, Ind.). A statistical analysis of data for the drug-treated groups compared to data for the vehicle group was performed using the one-way analysis of variance (ANOVA) with Dunnett's Multiple Comparisons test.

Following the procedure described above, the effect of topiramate on plasma glucose and triglyceride levels was determined for female diabetic db/db mice and littermates, following 11 days oral dosage, with results as listed in Table 3 and 4. Body weights are in Table 5. The abbreviation N represents the number of animals per study group.

TABLE 3

Plasma Glucose

| Treatment | Homozygous Diabetic Mice | | | Heterozygous Non-Diabetic Mice | | |
|---|---|---|---|---|---|---|
| | N | Plasma Conc. (mg/dL ± SEM) | % Change | N | Plasma Conc. (mg/dL ± SEM) | % Change |
| Vehicle | 8 | 525 ± 17 | — | 8 | 147 ± 4 | — |
| Topiramate 10 mg/kg | 8 | 382 ± 46 P < 0.05 | −27.4 | 7 | 145 ± 6 | −1.2 |
| Topiramate 30 mg/kg | 7 | 344 ± 31 P < 0.01 | −34.6 | 7 | 152 ± 6 | +3.8 |
| Topiramate 100 mg/kg | 8 | 333 ± 42 P < 0.01 | −36.6 | 8 | 148 ± 7 | +0.8 |
| Topiramate 300 mg/kg | 7 | 207 ± 41 P < 0.01 | −60.5 | 8 | 121 ± 7 P < 0.01 | −17.2 |

TABLE 4

Plasma Triglycerides

| Treatment | Homozygous Diabetic Mice | | | Heterozygous Non-Diabetic Mice | | |
|---|---|---|---|---|---|---|
| | N | Plasma Conc. (mg/dL ± SEM) | % Change | N | Plasma Conc. (mg/dL ± SEM) | % Change |
| Vehicle | 8 | 342 ± 20 | — | 8 | 141 ± 10 | — |
| Topiramate 10 mg/kg | 8 | 277 ± 30 | −18.9 | 7 | 141 ± 13 | −0.3 |
| Topiramate 30 mg/kg | 7 | 303 ± 29 | −11.2 | 7 | 116 ± 6 | −17.5 |
| Topiramate 100 mg/kg | 8 | 227 ± 15 P < 0.01 | −33.7 | 8 | 92 ± 6 P < 0.01 | −34.8 |
| Topiramate 300 mg/kg | 7 | 199 ± 16 P < 0.01 | −41.7 | 8 | 138 ± 15 | −1.8 |

TABLE 5

Body Weights

| Treatment | Homozygous Diabetic Mice | | Heterozygous Non-Diabetic Mice | |
|---|---|---|---|---|
| | N | Change in Body Weight (g ± SEM) | N | Change in Body Weight (g ± SEM) |
| Vehicle | 8 | 2.4 ± 0.5 | 8 | −0.7 ± 0.4 |
| Topiramate 10 mg/kg | 8 | 1.7 ± 0.9 | 7 | 0.5 ± 0.2 |
| Topiramate 30 mg/kg | 7 | 2.6 ± 1.0 | 7 | 0.0 ± 0.3 |
| Topiramate 100 mg/kg | 8 | 1.5 ± 0.7 | 8 | 0.2 ± 0.2 |
| Topiramate 300 mg/kg | 7 | 0.7 ± 2.4 | 8 | −2.2 ± 0.5 P < 0.05 |

The results show that topiramate decreased blood glucose in a dose-dependent manner by 27% (P<0.05 vs. control), 35% (P<0.01 vs. control), 37% (P<0.01 vs control), and 61% (P<0.01 vs control) for dosage levels of 10, 30, 100 and 300 mg/kg/day respectively. Topiramate dosing at 100 and 300 mg/kd/day also significantly (P<0.01) decreased plasma triglyceride levels by up to 42% versus diabetic controls. The results demonstrate that topiramate significantly ameliorates the diabetic condition of the homozygous diabetic mice and that this activity of topiramate is not dependent on a reduction in body weight.

EXAMPLE 3

Six week old male Zucker diabetic fatty (ZDF/Gmi-Fa) rats were purchased from Genetic Models, Inc. Indianapolis, Ind. The rats were housed in groups of four in hanging metal cages, at an ambient temperature of 68–72° F., on a 12 hour-12 hour light-dark schedule and given access to water and food ad libitum. Lean rats (ZDF/GMI–+/+or +/fa) were used as normal, non-diabetic controls. The diet was comprised of LabDiet 5008 breeding formula (PMI Nutrition Int'l, Brentwood, Mo.).

The vehicle, used as a reference and for test compounds, was 0.5% methylcellulose dissolved in water. The compounds were either fully dissolved or uniformly suspended in the vehicle when administered to the mice.

The rats were randomly separated into four groups of eight. The groups were as follows: one vehicle control group and three groups that each received one of three doses of TPM (30, 100, or 300 mg/kg, respectively). Topiramate or vehicle was administered orally by gavage once a day, for 14 consecutive days, during the $8^{th}$ hour of the light portion of the light-dark cycle.

At the start of the study, the rats were bled through a tail vein and plasma glucose and triglyceride levels were determined. Between 18 and 24 hours after the last dose was administered, blood samples were again taken via tail clip on day 1 (fed animals) and day 14 (fed animals). The plasma was collected into 2 mL heparinized snap-top polypropylene tubes, then placed in ice. Plasma was separated from blood cells by centrifugation (20 minutes at 1800 g). For samples not assayed immediately, the plasma was transferred into 96-well plates and frozen at −70° C.

Body weights for the animals were determined at the start of the study and again after 14 days oral dosing. Glucose and triglycerides were assayed using standard procedures for blood clinical laboratories. Specifically, the samples were analyzed using an automated Hitachi 717 autoanalyzer (Boehringer Mannheim/Hitachi 717 Autoanalyzer, Boehringer Mannheim Laboratory Systems Division, Indianapolis, Ind.). A statistical analysis of data for the drug-treated groups compared to data for the vehicle group was performed using the one-way analysis of variance (ANOVA) with Dunnett's Multiple Comparisons test.

Following the procedure described above, the effect of topiramate on plasma glucose, triglyceride levels and body weight changes was determined for male Zucker rats, orally dosed for 14 days, with results as listed in Table 6–8. The abbreviation N represents the number of animals per study group.

TABLE 6

Plasma Glucose Levels

| Treatment | N | Plasma Conc. (mg/dL) ± sem | % Change from Diabetic Control | % of Diabetic Control |
|---|---|---|---|---|
| Diabetic Vehicle Control | 8 | 329.6 ± 17.7 | | |
| Topiramate 30 mg/kg | 8 | 247.4 ± 17.8 P < 0.01 | −24.9 | 75.1 |
| Topiramate 100 mg/kg | 7 | 170.3 ± 14.7 P < 0.01 | −47.5 | 52.5 |
| Topiramate 300 mg/kg | 8 | 166.4 ± 11.1 P < 0.01 | −49.5 | 50.5 |

TABLE 7

Plasma Triglyceride Levels

| Treatment | N | Plasma Conc. (mg/dL) ± sem | % Change from Diabetic Control | % of Diabetic Control |
|---|---|---|---|---|
| Diabetic Control | 7 | 605.9 ± 40.1 | | |
| Topiramate 30 mg/kg | 7 | 482.4 ± 10.5 P < 0.05 | −20.4 | 79.6 |
| Topiramate 100 mg/kg | 7 | 498.6 ± 58.8 | −17.7 | 82.3 |
| Topiramate 300 mg/kg | 8 | 423.0 ± 33.6 P < 0.01 | −30.2 | 69.8 |

TABLE 8

Body Weight Change (grams)

| Treatment | N | Body Weight Change Gms ± sem |
|---|---|---|
| Diabetic Vehicle Control | 8 | +103.0 ± 2.1 |
| Topiramate, 30 mg/kg | 8 | +95.5 ± 7.2 |
| Topiramate, 100 mg/kg | 7 | +75.7 ± 2.7 (P < 0.01) |
| Topiramate, 300 mg/kg | 8 | +64.4 ± 6.0 (P < 0.01) |

As indicated by the data in the Tables above, topiramate decreased blood glucose levels by 25–50% (P<0.01). The reduction in blood glucose levels at 30 mg/kg/day occurred without significant body weight change. Topiramate at 30 and 300 mg/kg/day also decreased plasma triglyceride levels (20% and 30%; P<0.05 and P<0.01, respectively).

Collectively, the results from the db/db mice (Example 3) and the Zucker rats (Example 4) indicate that topiramate is an effective agent for the treatment of hyperglycemia, with beneficial effects on triglycerides, and utility in the treatment of the hallmarks of Type II diabetes mellitus in humans.

EXAMPLE 4

Female db/db mice (C57BLK S/J-m$^{+/+}$ Lepr$^{db}$ Jackson Labs, Bar Harbor, Me.), 7–8 weeks of age, were housed four per cage in solid-bottomed shoe box cages. Room temperature was maintained at 68–72° F. and humidity at 50–65%. Room lighting was on a 12-hour light/12-hour dark cycle. The mice were maintained on NIH Rat and Mouse/Auto 6F reduced fat diet #5K52 (PMI Nutrition Int'l Inc.). Food and water were supplied ad libitum.

Test compound and vehicle were dosed orally and prepared as suspensions in 0.5% hydroxypropylmethylcellulose (Dow Chemical, Midland, Mich.). The dosing volume was 10 mL/kg of body weight.

Different groups of female db/db mice (7–8/group) were orally gavaged daily for 11 days with either 0.5% methylcellulose in dH$_2$O (vehicle), topiramate at 30 or 100 mg/kg/day or 2,3:4,5-bis-O-(1-methylethylidene)-β-L-fructopyranose sulfamate (hereinafter referred to as Compound V) at 30 or 100 mg/kg/day. On day 10, the animals were fasted for 20 hours before being tested for oral glucose tolerance (OGT). On day 11, four hours after the final dose for each group, an oral glucose tolerance test (OGTT) was performed by oral glucose administration of 2 g/kg. Animals were bled through tail clip at 0 (before glucose), 30, 60 and 120 min after glucose challenge. The blood samples were collected into heparinized CB microvettes and then put on ice. The plasma samples will be assayed for plasma glucose determination by using SIGMA DIAGNOSTICS Trinder reagent (Sigma, St. Louis, Mo.). Statistical analysis was performed using the program Instat (Graphpad, Monrovia, Calif.) and performing one-way ANOVA with a Dunnett's multiple comparison test.

Following the above described procedure, the effect of topiramate and compound V on oral glucose tolerance in female db/db mice, 7 mice/group, was determined, with results as listed in Table 9. The abbreviation N represents the number of animals per study group.

TABLE 9

Oral Glucose Tolerance Test (fasted)

Plasma Glucose (mg/mL ± sem)

| Treatment | 0 min | 30 min | 60 min | 120 min |
|---|---|---|---|---|
| Vehicle | 260.5 ± 24.36 | 502.7 ± 45.5 | 448 ± 27 | 270.3 ± 23.8 |
| Topiramate 30 mg/kg | 188.43 ± 16.7 | 400.7 ± 68.4 | 294.8 ± 31.5 $P < 0.05$ | 124.1 ± 20 $P < 0.01$ |
| Topiramate 100 mg/kg | 159.5 ± 12.8 $P < 0.01$ | 454.3 ± 38.5 | 270.8 ± 52.6 $P < 0.05$ | 184.2 ± 32.3 |
| Compound V 30 mg/kg | 221.33 ± 22.9 | 440.8 ± 35.7 | 244.2 ± 21.6 $P < 0.01$ | 213.2 ± 28.7 |
| Compound V 100 mg/kg | 152.3 ± 27.3 $P < 0.01$ | 448.8 ± 42.6 | 319.4 ± 52.7 | 153 ± 33 $P < 0.05$ |

The results show that topiramate and compound V decreased fasting glucose levels and suppressed elevated blood glucose levels induced by oral glucose challenge. This suggests that topiramate and Compound V each improve glucose tolerance and may also increase insulin sensitivity.

Female ZDF rats were also randomly divided into control and topiramate (30 or 100 mg/kg/day) treated groups, dosed orally for 16 days, and tested for blood glucose levels and oral glucose tolerance following glucose challenge of 2 g/kg. The effect of topiramate was as listed in Table 10 (N=8 rats per treatment group).

TABLE 10

Plasma Glucose Levels (md/dL ± SEM)

| Treatment | Time = 0 | 60 Min after Challenge | 90 Min after Challenge | 120 Min after Challenge |
|---|---|---|---|---|
| Vehicle Control | 177.8 ± 17 | 474 ± 25 | 434 ± 25 | 357 ± 30 |
| Topiramate 30 mg/kg | 121 ± 13 | 342 ± 32 $P < 0.05$ | 269 ± 32 $P < 0.01$ | 206 ± 26 $P < 0.01$ |
| Topiramate 100 mg/kg | 129 ± 15 | 333 ± 32 $P < 0.01$ | 242 ± 28 $P < 0.01$ | 173 ± 23 $P < 0.01$ |

These results indicate that topiramate improves oral glucose tolerance at 60, 90 and 120 minutes after glucose challenge in ZDF rats. These data also show that oral administration of topiramate improves glucose tolerance and may also increase insulin sensitivity.

EXAMPLE 5

Five- to seven-week old male mice (ob/ob) were purchased from The Jackson Laboratory (Bar Harbor, Me.). Upon arrival the mice were quarantined for five days and housed individually in wire mesh cages with 2-inch square "nestlets". The mice were maintained at an ambient temperature of 21 to 23° C. on a 12 hour-12 hour light-dark schedule and given access to water and powdered chow ad libitum.

Topiramate was administered orally as a trace constituent in the food (0.143 to 2.54 mg/g). A precise quantity of topiramate was mixed thoroughly into a known amount of powdered lab chow using a mortar and pestle to grind the drug into the chow, after which the contents were placed in a 165 ounce lidded polyethylene tub and blended by shaking and rotating the tub. The lab chow (5002M Certified Diet Meal, manufactured in Brentwood, Mo. by Purina Mills, Inc.) was not less than 20% protein, 4.5% fat, and 64.5% CHO. The quantity of topiramate added to the food was based on the consumption of chow recorded during the previous three- or four-day period. The powdered food was put into stainless steel/aluminum feeders designed to prevent the mice from dispersing, spilling or contaminating the food. Mice that were able to disperse or soil the food were excluded from the study.

Thirty two-week old mice were randomly divided into three groups: (1) a control group in which no topiramate was added to the food, and (2) a group in which topiramate was added to the food in amounts sufficient to give a daily dose of 20 mg/kg for the entire 110-day dosing period, and (3) a group in which topiramate was added to the food in amounts sufficient to give a daily dose of 60 mg/kg for the entire dosing period.

The animals in each group were monitored for body weight, food consumption, blood glucose, HbA1C, insulin, triglycerides and physical signs of Type II diabetes mellitus or poor health. Body weight and food consumption were recorded twice-weekly on a Monday/Thursday or Tuesday/Friday schedule 8 to 12 hours into the light portion of the light-dark cycle. Body weight and food consumption were recorded using a scale designed for weights under 200 g. On each day body weight was recorded, the mice were observed for signs of Type II diabetes mellitus (skin lesions) or poor general health (e.g., lethargy or unkempt appearance). The mice were checked for skin lesions, and if present, the degree of severity was noted and recorded. If the general health of a mouse had deteriorated to a degree considered life threatening the mouse was euthanized.

Mice were allowed access to food containing topiramate until a few hours before being sacrificed by decapitation. Blood was collected from the neck wound into a parafilm-lined funnel. The blood was then transferred into beakers containing heparin. Plasma was separated from red blood cells by centrifugation. The plasma was frozen for subsequent analyses. Blood glucose levels, insulin and triglycerides were quantitated in the plasma. Glycated hemoglobin was also measured. The glycated hemoglobin required a 50 μl sample of whole blood, which was removed from the funnel before centrifugation. The plasma samples were then collected without freezing. All samples were packed in ice and shipped on the day blood was collected for overnight delivery to AniLytics, Inc. (200 Girard St., Suite 200, Gaithersburg, Md. 20877). The samples analyzed by AniLytics were assayed using standard procedures established by commercial laboratories that perform blood chemistry analyses. Statistical analysis was performed to determine if the data passed a test for normality (fit a Gaussian distribution). All groups were found to pass this test and therefore were further analysed using a test appropriate for parametric data, an unpaired two-tailed t-test (Prizm 2.01, Graph Pad Software, Inc.; San Diego, Calif. 92121). The data for a group of TPM-treated mice were compared to the control group.

Following the above described procedure, the effect of topiramate (TPM) on body weight (BW), glycated hemoglobin (HbA1C), blood glucose levels (BG), triglyceride and insulin levels in male ob/ob mice, were determined, with results as listed in Table 11. The abbreviation N represents the number of animals per group.

TABLE 11

Body Weight and Plasma Glucose Levels

|  | Control (n = 5) | TPM 20 mg/kg (n = 6) | TPM 60 mg/kg (n = 7) |
|---|---|---|---|
| BW (g) | 69.0 ± 4.9 | 65.6 ± 2.8 | 67.5 ± 1.6 |
| HbA1c (%) | 4.7 ± 0.4 | 4.98 ± 0.6 | 3.56 ± 0.4 |
| BG (mg/dL) | 243.2 ± 42.0 | 229.2 ± 46.0 | 144.3 ± 20.0 P < 0.05 |
| Triglycerides (mg/dL) | 111 ± 7.6 | 104 ± 6.4 | 88 ± 3.2 |
| Insulin (ng/mL) | 14.8 ± 8.6 | 12.2 ± 1.9 | 11.4 ± 2.1 |

The data show that topiramate treated animals (60 mg/kg) had consistently lower HbA1C and blood glucose (BG) levels when compared with control animals. These decreases were evident even without significant differences in body weight (BW).

Because the mice in this study were old when dosing was initiated there was already a high incidence of lesions. The initial total incidence of skin lesions was as follows: 47% of animals in control group when the study initiated; 38% of animals in the 20 mg/kg topiramate group, and 47% of animals in the 60 mg/kg TPM group.

During the first 60 days of dosing the total incidence of lesions gradually increased in the control group and usually ranged between 57% and 67%. During this period six mice in the control group died or had to be euthanized. In the group receiving 20 mg/kg of topiramate, the total incidence of lesions remained nearly constant during the first 60 days, usually ranging between 40% and 50%. During this period four mice in 20 mg/kg topiramate treated group died or had to be euthanized. The total incidence of lesions in the group treated with 60 mg/kg topiramate gradually declined, and after the first three weeks of dosing ranged between 15% and 38%. Two mice in the group treated with 60 mg/kg topiramate died during the first 60 days of dosing; both had severe lesions that already existed before dosing was initiated.

During the dosing period between 62 and 110 days, the total incidence of lesions in the 60 mg/kg/day topiramate treated group was lower than in the control group.

Thus, the data show that topiramate improved glycemic control, reduced triglycerides, and may increase insulin sensitivity in the absence of a decrease in body weight. Topiramate also reduced the incidence and prevalence of skin lesions in animals that exhibited these lesions before topiramate dosing was initiated.

Based on the results reported in the Examples above, it can be concluded that compounds of formula (I) are useful in preventing the development of Type II diabetes mellitus in mammals including humans.

For preventing the development of Type II diabetes mellitus or Syndrome X a compound of formula (I) may be employed by administering a therapeutically effective amount of the compound of formula 1. More particularly, for preventing the development of Type II diabetes mellitus or Syndrome X a compound of formula (I) may be employed by administering repeated oral doses in the range of about 10 to 1000 mg daily, preferably in the range of about 10 to 650 mg daily, more preferably in the range of about 16 to 325 mg once or twice daily.

As used herein, the term "composition" is intended to encompass a product comprising the specified ingredients in the specified amounts, as well as any product which results, directly or indirectly, from combinations of the specified ingredients in the specified amounts.

As used herein, unless otherwise noted, the term "therapeutically effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Optimal dosages to be administered may be readily determined by those skilled in the art, and will vary with the mode of administration, the strength of the preparation and the advancement of the disease condition. In addition, factors associated with the particular patient being treated, including patient's sex, age, weight, diet, physical activity, time of administration and concomitant diseases and medications, may result in the need to adjust dosages.

For pharmaceutical administration, one or more of the compounds of formula (I) may be administered by any suitable means, as would be apparent to one skilled in the art. More particularly, the compound(s) of formula (I) may be administered by any parenteral method, including, but not limited to oral, pulmonary, intraperitoneal (ip), intravenous (iv), intramuscular (im), subcutaneous (sc), transdermal, buccal, nasal, sublingual, ocular, rectal and vaginal. It will be readily apparent to those skilled in the art that any dose or frequency of administration that provides the therapeutic effect described herein is suitable for use in the present invention.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., i.v. sterile injectable formulations will be prepared using appropriate solubilizing agents. A unit dose would contain about 10 to 200 mg of the active ingredient. Topiramate is currently available for oral administration in round tablets containing 25 mg, 100 mg or 200 mg of active agent. The tablets contain some or all of the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method for treating skin lesions associated with Type II diabetes mellitus or Syndrome X comprising administering to a mammal in need thereof a therapeutically effective amount of a compound of the formula I:

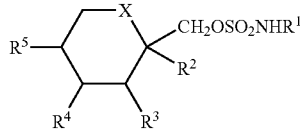

(I)

wherein

X is $CH_2$ or oxygen;

$R^1$ is hydrogen or alkyl; and $R^2$, $R^3$, $R^4$ and $R^5$ are independently hydrogen or lower alkyl and, when X is $CH_2$, $R^4$ and $R^5$ may be alkene groups joined to form a benzene ring and, when X is oxygen, $R^2$ and $R^3$ and/or $R^4$ and $R^5$ together may be a methylenedioxy group of the following formula (II):

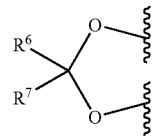

(II)

wherein $R^6$ and $R^7$ are the same or different and are hydrogen, lower alkyl or are alkyl and are joined to form a cyclopentyl or cyclohexyl ring.

2. The method of claim 1, wherein the compound of formula (I) is topiramate.

3. The method of claim 1, wherein the therapeutically effective amount is from about 10 to 1000 mg daily.

4. The method of claim 1, wherein the therapeutically effective amount is from about 10 to 650 mg daily.

5. The method of claim 1, wherein the amount is of from about 16 to 325 mg once or twice daily.

* * * * *